United States Patent
Ooishi et al.

(10) Patent No.: US 7,926,323 B2
(45) Date of Patent: Apr. 19, 2011

(54) THERMAL CONDUCTIVITY MEASURING METHOD AND APPARATUS, AND GAS COMPONENT RATIO MEASURING APPARATUS

(75) Inventors: Yasuharu Ooishi, Tokyo (JP); Shigeru Aoshima, Tokyo (JP); Nobuyoshi Shingyouji, Tokyo (JP); Yasue Hayashi, Tokyo (JP); Shuji Morio, Tokyo (JP)

(73) Assignee: Yamatake Corporation, Tokyo (JP)

( * ) Notice: Subject to any disclaimer, the term of this patent is extended or adjusted under 35 U.S.C. 154(b) by 460 days.

(21) Appl. No.: 12/088,225

(22) PCT Filed: Sep. 25, 2006

(86) PCT No.: PCT/JP2006/318987
§ 371 (c)(1),
(2), (4) Date: Mar. 26, 2008

(87) PCT Pub. No.: WO2007/037209
PCT Pub. Date: Apr. 5, 2007

(65) Prior Publication Data
US 2009/0277246 A1    Nov. 12, 2009

(30) Foreign Application Priority Data
Sep. 27, 2005  (WO) .................. PCT/JP2005/017748

(51) Int. Cl.
*G01N 25/18*     (2006.01)
(52) U.S. Cl. ...................................... 73/25.03
(58) Field of Classification Search ............. 73/25.03
See application file for complete search history.

(56) References Cited

U.S. PATENT DOCUMENTS

| 4,944,035 | A |   | 7/1990 | Aagardl et al. |
| 5,494,826 | A | * | 2/1996 | Stetter et al. .................. 436/147 |
| 5,756,878 | A |   | 5/1998 | Muto et al. |
| 6,132,083 | A |   | 10/2000 | Enala |
| 2005/0025215 | A1 |   | 2/2005 | Arndt et al. |

FOREIGN PATENT DOCUMENTS

| JP | 2797198 | B2 | 7/1998 |
| JP | 10-508382 | A | 8/1998 |
| JP | 3114139 | B2 | 9/2000 |
| JP | 3153787 | B2 | 1/2001 |
| JP | 2001-221758 | A | 8/2001 |
| JP | 2005-505758 | A | 2/2005 |

* cited by examiner

*Primary Examiner* — Hezron Williams
*Assistant Examiner* — Rodney T Frank
(74) *Attorney, Agent, or Firm* — Holtz, Holtz, Goodman & Chick, PC

(57) ABSTRACT

A heat radiation coefficient C [=Ph/(Th−To)] from a microheater is calculated in accordance with a power Ph applied to the microheater which is supported in air and provided in an ambient gas, a heater temperature Th, and an ambient temperature To at this moment. Further, a thermal conductivity $\lambda_{(T)}$ of the ambient gas is obtained from the calculated heat radiation coefficient C based on a proportional relation $[C=K\cdot\lambda_{(T)}]$ between a thermal conductivity $\lambda_{(T)}$ of the ambient gas and the heat radiation coefficient C at a measurement temperature T [=(Th−To)/2].

10 Claims, 9 Drawing Sheets

FIG. 5

| SAMPLE | METHANE | PROPANE | NITROGEN |
|---|---|---|---|
| GAS 1 | 80 | 10 | 10 |
| GAS 2 | 90 | 5 | 5 |
| GAS 3 | 95 | 2.5 | 2.5 |
| GAS 4 | 100 | 0 | 0 |
| GAS 5 | 80 | 5 | 15 |
| GAS 6 | 90 | 2 | 8 |
| GAS 7 | 95 | 1 | 4 |
| GAS 8 | 80 | 15 | 5 |
| GAS 9 | 90 | 8 | 2 |
| GAS 10 | 95 | 4 | 1 |

THERMAL CONDUCTIVITY MEASURING METHOD AND APPARATUS, AND GAS COMPONENT RATIO MEASURING APPARATUS

This application is a U.S. National Phase Application under 35 USC 371 of International Application PCT/JP2006/318987 filed Sep. 25, 2006.

TECHNICAL FIELD

The present invention relates to thermal conductivity measuring method and apparatus that can readily measure a thermal conductivity of a gas whose type is known but whose component ratios (composition ratios) are unknown, e.g., a natural gas, and a gas component ratio measuring apparatus using the thermal conductivity measuring apparatus.

BACKGROUND ART

As a technique of measuring a thermal conductivity of a gas, driving a heater at a fixed temperature in a state where an ambient gas surrounding the heater is maintained at the fixed temperature and measuring a calorific value of the heater is known. This technique utilizes the fact that a calorific value of the heater is in proportion to a thermal conductivity of the ambient gas. However, when adopting this technique to measure a thermal conductivity of the ambient gas, this technique cannot help having a large-scale structure because, e.g., a constant-temperature bath that maintains the ambient temperature at a fixed temperature is required.

Further, Japanese Patent Application Laid-open No. 2001-221758 discloses that providing a cavity that have a fluid accumulated therein so as to face a flow path along which the fluid is led and also providing a porous body at a boundary of this cavity and the flow path enables accurately detecting a thermal conductivity of the fluid from a calorific value of a sensor (a heater) assembled in the cavity. It is to be noted that the porous body is designed so that the fluid in the flow path is exchanged with the fluid in the cavity by molecular diffusion alone.

However, since a thermal conductivity of a gas generally has intrinsic temperature change characteristics according to a type of this gas, there is a fundamental problem that the thermal conductivity cannot be accurately measured by simply measuring a calorific value of a heater. In particular, when a mixed gas in which a plurality of types of gases are mixed like a natural gas is an ambient gas, measuring its thermal conductivity is very difficult.

It is to be noted that there is also adopted a technique of passing a mixed gas to a member called a column, utilizing a difference in flow velocity due to a difference in molecular weight of gases to analyze composition ratios, and measuring a thermal conductivity of the mixed gas. However, such a technique has a problem that analysis of the composition ratios of the mixed gas by using the column requires a long time and an entire structure of an analysis apparatus is completed and expensive, for example.

DISCLOSURE OF INVENTION

It is an object of the present invention to provide thermal conductivity measuring method and apparatus that can readily measure a thermal conductivity of a pure gas or a mixed gas. Further, it is an object of the present invention to provide a gas component ratio measuring apparatus that can obtain composition ratios of a mixed gas whose type is known, e.g., a natural gas to evaluate a calorific value by using the thermal conductivity measuring method and apparatus.

The present invention pays notice to the fact that, when a heater with a small heat radiation area which is called a microheater, i.e., a heater which can be regarded as a thermal point source is driven and a thermal conductivity of an ambient gas is measured based on a calorific value of this heater, the ambient gas near the heater can thereby form a local temperature distribution to enter an equilibrium state without producing a natural convection, and an average heat transfer coefficient h at this time is substantially in proportion to a thermal conductivity $\lambda$ of the ambient gas and in inverse proportion to a thickness d of a temperature boundary layer. Further, it also pays notice to the fact that the thermal conductivity $\lambda$ of the ambient gas and a heat radiation coefficient C from the microheater have a high correlation.

Therefore, a thermal conductivity measuring method according to the present invention uses a microheater which is supported in air and provided in an ambient gas (a measurement target) to measure a thermal conductivity of the ambient gas from a calorific value of the heater, and it is particularly characterized in that a heat radiation coefficient C [=Ph/(Th−To)] from the microheater is calculated based on a power Ph applied to the microheater, a heater temperature Th, and an ambient temperature To at this moment, and a thermal conductivity $\lambda_{(T)}$ of the ambient gas at a measurement temperature T is obtained from the calculated heat radiation coefficient C in accordance with a proportional relation [C=K·$\lambda_{(T)}$] between the thermal conductivity $\lambda_{(T)}$ of the ambient gas and the heat radiation coefficient C at the measurement temperature T.

It is to be noted that the measurement temperature T is obtained as an average temperature [=(Th+To)/2] of the heater temperature Th and the ambient temperature To. Furthermore, the proportional relation [C=K·$\lambda_{(T)}$] of the thermal conductivity $\lambda_{(T)}$ of the ambient gas and the heat radiation coefficient C at the measurement temperature T is obtained as a relational expression [C=2·($\lambda_{(T)}$/d)·S] representing the heat radiation coefficient C by using the thermal conductivity $\lambda_{(T)}$ of the ambient gas at the measurement temperature T, a thickness d of a temperature boundary layer of the ambient gas acquired with a thermal conductivity of a reference gas and a thickness of its temperature boundary layer being determined as references, and a heat radiating area S of the microheater on the assumption that an average thermal conductivity h from the microheater to the ambient gas is in proportion to a thermal conductivity $\lambda$ of the ambient gas and in inverse proportion to the thickness d of the temperature boundary layer of the ambient gas.

A thermal conductivity measuring apparatus which executes such a thermal conductivity measuring method is realized by comprising: a microheater which is supported in air and provided in an ambient gas; heater temperature detecting means for obtaining a temperature Th of the microheater; a temperature sensor which measures an ambient temperature To of the microheater; a power supply which energizes the microheater to generate heat; heat radiation coefficient computing means for calculating a heat radiation coefficient C from the microheater as [C=Ph/(Th−To)] in accordance with an energization power Ph for the microheater from the power supply, the heater temperature Th, and the ambient temperature To at this moment; measurement temperature calculating means for obtaining a measurement temperature of the ambient gas in accordance with the heater temperature Th and the ambient temperature To; and thermal conductivity computing means for obtaining a thermal conductivity $\lambda_{(T)}$ of the ambient gas at the measurement temperature T from the heat radiation coefficient C calculated by the heat radiation coefficient computing means based on a proportional relation [$C = K \cdot \lambda_{(T)}$] between the thermal conductivity $\lambda_{(T)}$ of the ambient gas and the heat radiation coefficient C at the measurement temperature T.

At this time, it is good enough to configure the heater temperature detecting means to calculate the heater temperature Th from, e.g., a resistance value Rstd of the microheater at a standard temperature and a resistance value Rh of the heater obtained from the driving power Ph and an energization current Ih when the power supply energizes the microheater to generate heat or a terminal voltage Vh and the energization current Ih. Moreover, it is good enough to configure the thermal conductivity computing means to obtain the thermal conductivity $\lambda_{(T)}$ associated with the heat radiation coefficient C acquired by the heat radiation coefficient computing means by making reference to a table in which the proportional relation between the thermal conductivity $\lambda_{(T)}$ of the ambient gas and the heat radiation coefficient C at the measurement temperature T is registered.

Additionally, it is also preferable to comprise measurement condition changing means for changing the power Ph applied to the microheater to vary the heater temperature Th.

Further, a gas component ratio measuring apparatus according to the present invention is characterized by comprising: means for obtaining a thermal conductivity % (T of an ambient gas at each of different heater temperatures by using the thermal conductivity measuring apparatus; and analyzing means for analyzing composition ratios of the ambient gas based on a simultaneous equation of the thermal conductivity $\lambda_{(T)}$ at each of the heater temperatures.

Specifically, the analyzing means is configured to obtain the composition ratios by analyzing [n–1] thermal conductivities $\lambda_{(T1)}$, and $\lambda_{(T2)}$ to $\lambda_{(Tn-1)}$ acquired at heater temperatures Th(1), and Th(2) to Th(n–1) set on [n–1] stages on the assumption that the ambient gas is a mixed gas containing n types of gases and the thermal conductivity $\lambda_{(T)}$ of the mixed gas is obtained by adding thermal conductivities $\lambda 1_{(T)}$, and $\lambda 2_{(T)}$ to $\lambda n_{(T)}$ of the respective gases at ratios determined in accordance with composition ratios and coupling coefficients of the respective gases.

It is to be noted that a coupling coefficient is used in, e.g., a Wassiljewa's expression for obtaining a thermal conductivity. Furthermore, this coupling coefficient can be obtained by, e.g., a Lindsay-Bromley's approximate expression as will be explained later.

Moreover, it is also useful to provide a function that obtains a calorific value of the ambient gas based on the composition ratios of the ambient gas acquired by the analyzing means to the gas component ratio measuring apparatus. It is to be noted that the ambient gas is constituted of a natural gas mainly containing methane, ethane, propane, and butane.

BRIEF DESCRIPTION OF DRAWINGS

FIG. 5 is a view showing examples of mixed gases having different composition ratios;

BEST MODES FOR CARRYING OUT THE INVENTION

A thermal conductivity measuring method, a thermal conductivity measuring apparatus, and a gas component ratio measuring apparatus according to the present invention will now be explained hereinafter with reference to the accompanying drawings.

Figure 1:
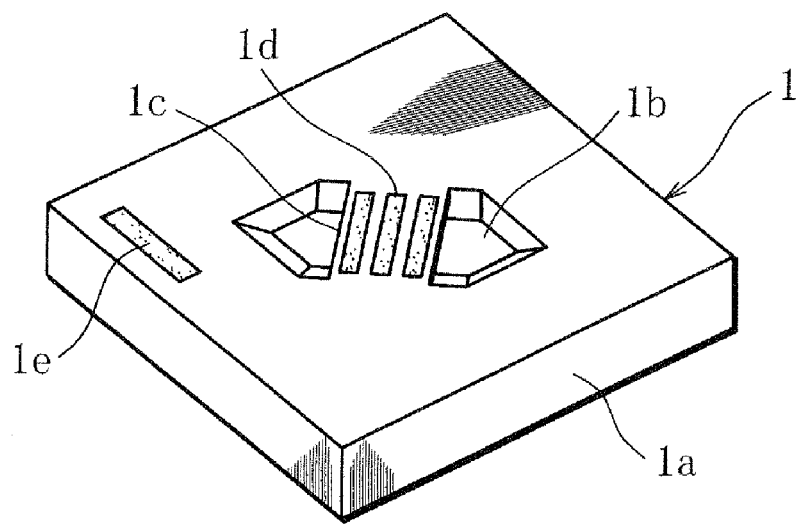
FIG. 1 is a view showing an element structure of a microheater used in the present invention.

According to the present invention, for example, a microheater 1 whose outline structure is shown in FIG. 1 is used to basically measure a thermal conductivity of an ambient gas (a pure gas or a mixed gas) from a calorific value of the microheater 1. In the microheater 1, a concave cavity 1b is formed on a surface of a silicon chip 1a having, e.g., a diameter of 0.5 mm and a dimension of approximately 1.5 mm square, a bridge is thrown over this cavity 1b to form a thin-film-like diaphragm 1c, and a small heat generating resistive element (a heater) 1d formed of, e.g., platinum is provided on this diaphragm 1c. Further, a temperature sensor 1e that measures an ambient temperature is generally provided at a peripheral portion of the silicon chip 1a.

Figure 2:
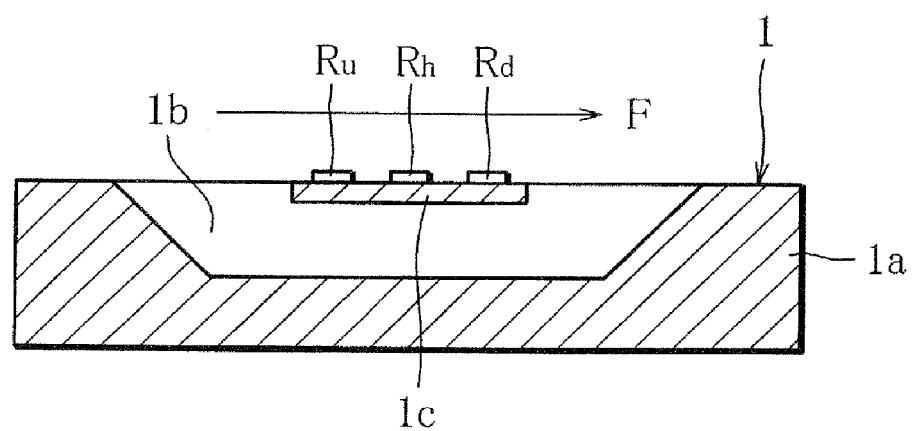
FIG. 2 is a view showing a schematic cross-sectional structure of the microheater.

As shown in, e.g., a schematic cross-sectional structural view of FIG. 2, a structure of such a microheater 1 is well known as a thermal flowmeter in which a pair of temperature sensors Ru and Rd are provided to sandwich a heater element Rh corresponding to the heat generating resistive element 1d along a flow direction F of a fluid. It is to be noted that each of the heat generating resistive element (the heater) 1d, an upstream-side temperature sensor Ru, a downstream-side temperature sensor Rd, and the ambient temperature sensor We provided on the surface of the silicon chip 1a is formed of, e.g., a thin film body of platinum. Furthermore, each of the heat generating resistive element (the heater) 1d, the temperature sensors Ru and Rd, and others is covered with an electric insulating film formed of, e.g., a thin silicon oxide ($SiO_2$) film or silicon nitride (SiN) film having a thickness of approximately 0.2 to 0.5 μm, thereby protecting its surface.

In particular, the heat generating resistive element (the heater) 1d forming a primary portion of the microheater 1 is sandwiched between the thin diaphragm 1c and the electric insulating film so that it is substantially supported in air to be positioned in an ambient gas. As a result, a front surface of the heat generating resistive element (the heater) 1d is in contact with the ambient gas through the electric insulating film, and a back surface of the same is in contact with the ambient gas through the diaphragm 1c. However, since each of the electric insulating film and the thin-film-like diaphragm is very thin, the front and back surfaces of the heat generating resistive element (the heater) 1d can be considered to be substantially in contact with the ambient gas. In the following description, the heat generating resistive element (the heater) 1d itself is explained as the microheater 1.

Meanwhile, the microheater 1 formed of the heat generating resistive element of, e.g., platinum has properties that its resistance value varies depending on a temperature and, when the resistance value at a standard temperature Tstd of, e.g., 20° C. is Rstd, assuming that a primary resistance-temperature coefficient is α and a secondary resistance-temperature coefficient is β, a resistance value Rh at a temperature Th is given as the following expression:

$$Rh = Rstd \cdot \{1 + \alpha(Th - Tstd) + \beta(Th - Tstd)^2\} \quad (1)$$

Moreover, based on a power Ph and an energization current Ih for energizing and driving the microheater 1, the resistance value Rh of the microheater 1 can be obtained as represented by the following expression:

$$Rh = Ph/Ih^2 \quad (2)$$

Alternatively, based on an end-to-end voltage Vh of the microheater 1 and the energization current Ih at this moment, the resistance value Rh can be obtained as represented by the following expression:

$$Rh = Vh/Ih \quad (3)$$

Additionally, the temperature Th of the microheater 1 is stabilized when it enters a thermal equilibrium state with the ambient gas. Further, assuming that a heat radiation coefficient C from the microheater 1 to the ambient gas is C, the driving power Ph of the microheater 1 in this equilibrium state have the following relationship with the heater temperature Th and an ambient temperature To:

$$C \cdot (Th - To) = Ph \quad (4)$$

In other words, when conditions satisfying Expression (4) are achieved, the microheater 1 and the ambient gas enter the thermal equilibrium state to be stabilized. Therefore, based on the conditions for this thermal equilibrium state, the heat radiation coefficient C from the microheater 1 to the ambient gas can be obtained as represented by the following expression:

$$C = Ph/(Th - To) \quad (4a)$$

Specifically, as mentioned above, the heater temperature Th can be obtained by calculating the resistance value Rh of the microheater 1 from the driving power Ph of the microheater 1 and the energization current Ih at this moment or from the end-to-end voltage Vh of the microheater 1 and the energization current Ih of the same and back-calculating Expression (1) from this resistance value Rh. Furthermore, as in the explanation of the structure of the microheater 1 by using, e.g., FIG. 1, the ambient temperature To can be obtained by utilizing the ambient temperature detection temperature sensor 1e provided near the microheater 1. Therefore, respectively obtaining the driving power Ph of the microheater 1, the heater temperature Th of the microheater 1, and the ambient temperature To of the same enables calculating the heat radiation coefficient C from the microheater 1 to the ambient gas in accordance with Expression (4).

On the other hand, assuming that an average heat transfer coefficient (in movement of heat from an object as a heat source to the ambient gas, when a heat radiating surface of the heat source is divided into a plurality of blocks, a heat transfer coefficient in each block is referred to as a local heat transfer coefficient, and a heat transfer coefficient of all the blocks (i.e., the entire heat radiating surface of the heat source) obtained by averaging the local heat transfer coefficients of the respective blocks is referred to as an average heat transfer coefficient) from the microheater 1 to the ambient gas is h and a heat radiating area of the microheater 1 is S, the heat radiation coefficient C can be generally represented as follows:

$$C = 2 \cdot h \cdot S \quad (5)$$

It is to be noted that the average heat transfer coefficient h varies depending on a situation of a natural convection of the ambient gas or a surface state of the microheater 1. Moreover, in the coefficient [2], the fact that heat transfer from the microheater 1 to the ambient gas is carried out on each of both the front and back surfaces of the microheater 1 is considered as depicted in FIG. 3 schematically showing its concept.

Figure 3:
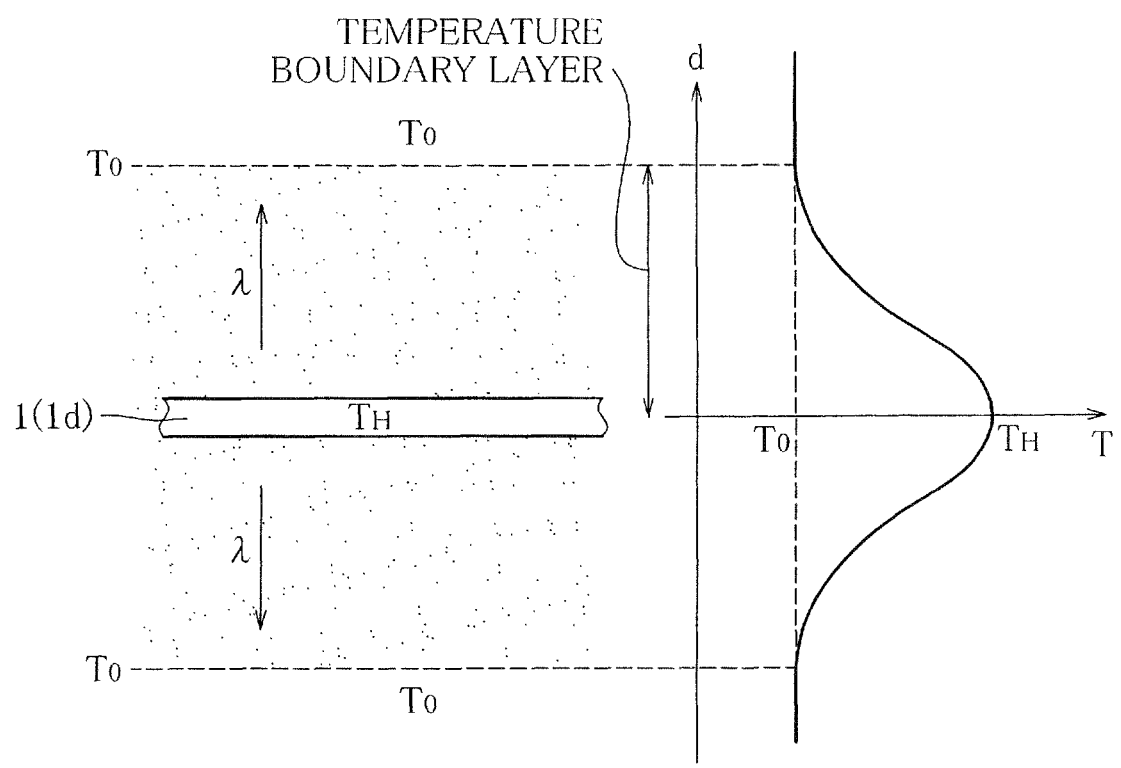
FIG. 3 is a view schematically showing a temperature distribution of an ambient gas near the microheater when the microheater is driven to generate heat.

However, since an element area (a heat radiating area) of the microheater 1 is small, if a range of a temperature change caused due to heat generation of this microheater 1 is small, a spot-like temperature change alone occurs, and a natural convection of the ambient gas is not produced, a distribution of a temperature around the microheater 1 is gradually lowered as distanced from the microheater 1 as exclusively shown in FIG. 3. In particular, a temperature of the ambient gas in a region that is in contact with the microheater 1 is increased to the heater temperature Th and also gradually reduced to the ambient temperature To as distanced from the microheater 1.

Defining a distance along which a temperature of the ambient gas near the microheater 1 that forms such a temperature distribution is reduced from the heater temperature Th to the ambient temperature To as a thickness d of a temperature boundary layer, it can be considered that the average heat transfer coefficient h is in proportion to a thermal conductivity λ of the ambient gas and in inverse proportion to the thickness d of the temperature boundary layer. That is, the average heat transfer coefficient h is determined as follows:

$$h = \lambda/d \quad (6)$$

It is to be noted that the thermal conductivity λ of the ambient gas generally tends to increase as a temperature rises. For example, a thermal conductivity $\lambda_{(T)}$ of the ambient gas at an average temperature T of the temperature boundary layer is given as represented by the following expression:

$$\lambda_{(T)} = \lambda o (1 + \gamma \cdot T) \quad (7)$$

In this expression, λo is a thermal conductivity of the ambient gas at a reference temperature (e.g., 0° C.), and γ is a primary temperature coefficient. Additionally, the average temperature T of the temperature boundary layer is given as represented by, e.g., the following expression:

$$T = (Th + To)/2$$

Further, the thickness d of the temperature boundary layer varies depending on the thermal conductivity λ of the ambient gas, and the thickness d is reduced since heat transfer becomes faster as the thermal conductivity λ is increased. Contrarily, when the thermal conductivity λ of the ambient gas is small, a gradient of a temperature change becomes gentle since heat transfer is slow, and the thickness d of the temperature boundary layer is thereby increased. Furthermore, assuming that a thermal conductivity of a reference gas at a reference temperature Tstd is λstd and a thickness of the temperature boundary layer at this moment is given as dstd, the following relationship is achieved with respect to a thickness do of the temperature boundary layer of the ambient gas having a thermal conductivity λo at the reference temperature Tstd:

$$do \cdot \lambda = dstd \cdot \lambda std \quad (8a)$$

It is to be noted that the reference gas means an arbitrarily selected gas, and a methane gas is selected as the reference gas in this embodiment, for example.

Furthermore, the following relationship is achieved between the thickness do of the temperature boundary layer of the ambient gas having the thermal conductivity λo at the reference temperature Tstd, a thermal conductivity $\lambda_{(T)}$ of the ambient gas at a temperature (a measurement temperature) T, and a thickness $d_{(T)}$ of the temperature boundary layer at this moment:

$$do \cdot \lambda o = d_{(T)} \cdot \lambda_{(T)} \quad (8b)$$

That is, it can be considered that a product of the thickness d of the temperature boundary layer and the thermal conductivity λ of the ambient gas is constant irrespective of a type of a gas.

In other words, the thickness $d_{(T)}$ of the temperature boundary layer in the ambient gas at the measurement temperature T can be given as presented by the following expression:

$$d_{(T)} = dstd \cdot \lambda std / \lambda_{(T)} \quad (8c)$$

Moreover, a heat radiating area S of the microheater 1 generally often means an entire area of the diaphragm 1c having the heat generating resistive element (the heater) 1d formed thereon, and a temperature distribution of the ambient gas near the microheater 1 varies in dependence on a temperature distribution on the diaphragm 1c. However, in case of an ambient gas having a large thermal conductivity λ, since its temperature distribution has a sharp shape, the substantial heat radiating area S of the microheater 1 can be considered as an area smaller than an area So of the diaphragm 1c.

Specifically, the substantial heat radiating area S of the microheater 1 is reduced in inverse proportion to the thermal conductivity $\lambda_{(T)}$ of the ambient gas in the temperature boundary layer, the substantial heat radiating area S can be considered as follows:

$$S \propto So / \lambda_{(T)} \quad (9)$$

Additionally, the heat radiating area S of the microheater 1 has a spot-like shape in corporation with the fact that the microheater 1 itself is small, and hence it can be considered that the heal radiating area S substantially serves as a thermal point source.

Summarizing the relationship between the heat radiating coefficient C and the thermal conductivity $\lambda_{(T)}$ of the ambient gas based on the above-explained considerations, the following relationship can be derived from Expressions (5) to (8):

$$\begin{aligned} C &= 2 \cdot h \cdot S \\ &= 2 \cdot (\lambda_{(T)} / d_{(T)}) \cdot S \\ &= 2 \cdot S \cdot \lambda_{(T)} / [dstd \cdot \lambda std / \lambda_{(T)}] \\ &= 2 \cdot S \cdot \lambda_{(T)}^2 / [dstd \cdot \lambda std] \end{aligned} \quad (10)$$

Further, assigning Expression (9) to this Expression (10) enables deriving the following relationship:

$$C \propto 2 \cdot [(So / \lambda_{(T)}) \cdot \lambda_{(T)}^2 / [dstd \cdot \lambda std]$$
$$\propto 2 \cdot So \cdot \lambda_{(T)} / d[dstd \cdot \lambda std] \quad (11)$$

Moreover, since the thermal conductivity λstd of the reference gas (e.g., a methane gas) at the reference temperature Tstd and the thickness dstd of the temperature boundary layer are already known and the area So of the diaphragm 1c is also already known, it can be read from Expression (11) that the heat radiation coefficient C is in proportion to the thermal conductivity $\lambda_{(T)}$ of the ambient gas at the measurement temperature T.

Thus, the present invention is characterized by obtaining the thermal conductivity $\lambda_{(T)}$ of the ambient gas at the measurement temperature T from the proportional relation between the heat radiation coefficient C and the thermal conductivity $\lambda_{(T)}$ in accordance with the heat radiation coefficient C acquired from the driving power Ph of the microheater 1.

Figure 4:
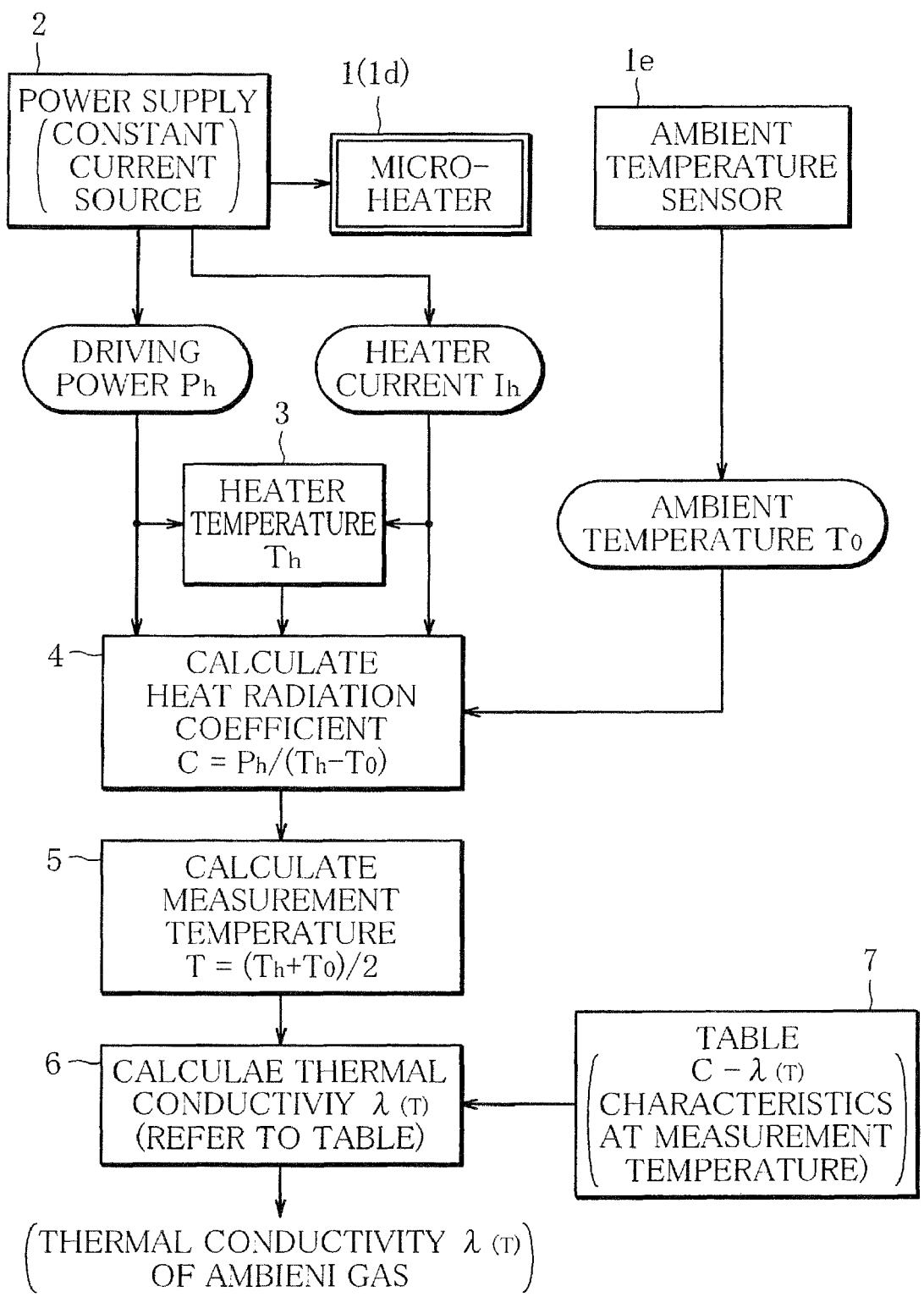
FIG. 4 is a schematic block diagram of a primary part of thermal conductivity measuring method and apparatus according to an embodiment of the present invention.

FIG. 4 is a conceptual view showing an embodiment of the present invention, in which reference numeral 1 (1d) denotes a microheater; 2, a power supply (e.g., a constant current source) for driving the microheater 1 to generate heat; and 1e, a temperature sensor that detects an ambient temperature of the microheater 1. The thermal conductivity measuring method and apparatus according to the present invention include heater temperature detecting means 3 for obtaining a heater temperature Th in accordance with a driving power Ph of the microheater 1 driven by the power supply 2 to generate heat and an energization current Ih at this moment as explained above, and also include heat radiation coefficient calculating means 4 for obtaining a heat radiation coefficient C from the microheater 1 in accordance with the heater temperature Th, an ambient temperature To acquired by the temperature sensor le, and the driving power Ph of the microheater 1. Calculation of the heat radiation coefficient C by this heat radiation coefficient calculating means 4 is carried out by executing the arithmetic operation [C=Ph/(Th−To)] as explained above.

Additionally, measurement temperature calculating means 5 obtains a measurement temperature T as an average temperature T [=(Th+To)/2] of a temperature boundary layer in accordance with the heater temperature Th and the ambient temperature To acquired by the temperature sensor 1e. Further, thermal conductivity calculating means 6 makes reference to a table 7 in accordance with the heat radiation coefficient C obtained by the heat radiation coefficient calculating means 4 at the measurement temperature T to acquire a thermal conductivity $\lambda_{(T)}$ associated with the heat radiation coefficient C from a relationship between the heat radiation coefficient C and the thermal conductivity $\lambda_{(T)}$ previously registered in the table 7, and outputs the obtained result.

The present inventors prepared a plurality of types of mixed gas shown in FIG. 5 containing methane, propane, and nitrogen to verify reliability of the thermal conductivity $\lambda_{(T)}$ of the ambient gas acquired as explained above, and examined the relationship between the thermal conductivity λ and the heat radiation coefficient C of each gas. It is to be noted that a first mixed gas has composition ratios of 80% of methane, 10% of propane, and 10% of nitrogen and a second mixed gas has composition ratios of 90% of methane, 5% of propane, and 5% of nitrogen in FIG. 5, for example. That is, each of these mixed gases is a sample of a gas whose type is known but whose component ratios (the composition ratios) are unknown.

Figure 6:
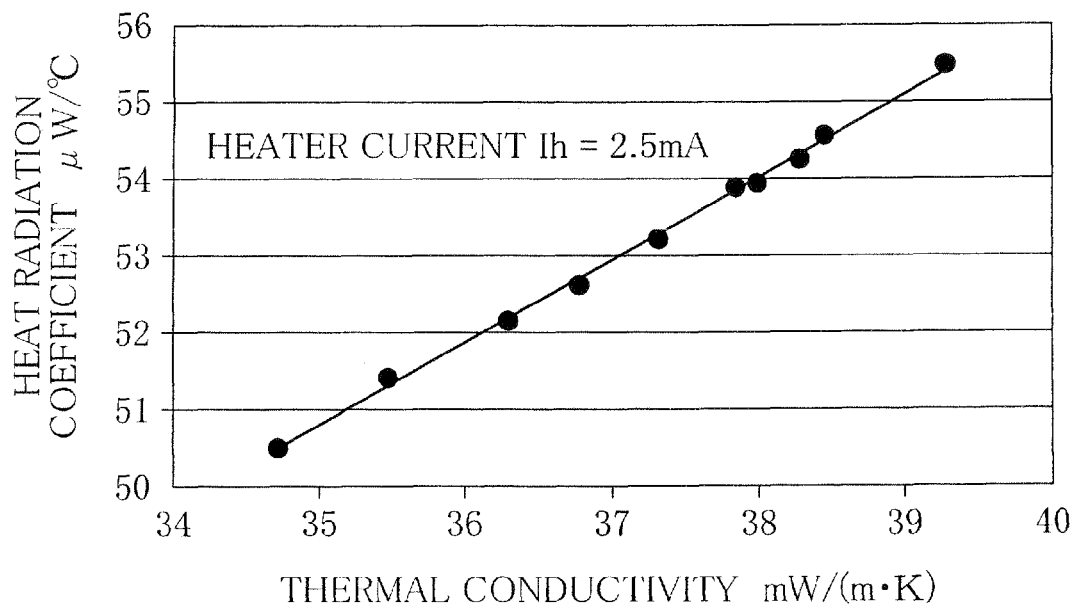
FIG. 6 is a view showing a relationship between a heat radiation coefficient C and a thermal conductivity $\lambda_{(T)}$ of an ambient gas at a measurement temperature T.

Further, when a current Ih of 2.5 mA was flowed to the microcomputer 1 in a situation where each of these mixed gases was used as an ambient gas to examine a relationship between the heat radiation coefficient C and the thermal conductivity $\lambda_{(T)}$ of each of these gases at this moment, a result depicted in FIG. 6 was obtained. It is to be noted that a temperature (a measurement temperature) T of the ambient gas in this example can be regarded as an average temperature [(Th+To)/2] in the temperature boundary layer. Furthermore, this experimental result shows that the thermal conductivity $\lambda_{(T)}$ of the mixed gas (the ambient gas) at the measurement temperature T and the heat radiation coefficient C have a substantially proportional relation. Therefore, it was confirmed that obtaining the heat radiation coefficient C as explained above enables directly evaluating the thermal conductivity $\lambda_{(T)}$ of the ambient gas from this heat radiation coefficient C.

Figure 7:
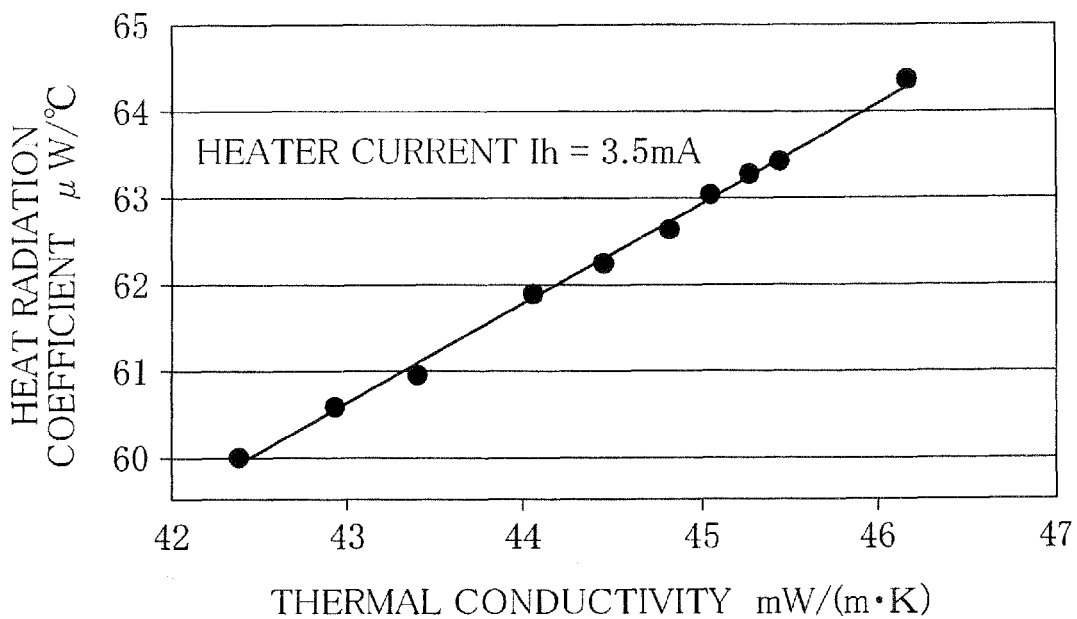
FIG. 7 is a view showing a relationship between the heat radiation coefficient C and the thermal conductivity $\lambda_{(T)}$ when the measurement temperature T is changed.

Furthermore, FIG. 7 shows a relationship between the heat radiation coefficient C and the thermal conductivity $\lambda_{(T)}$ of each of the mixed gases when the current Ih that is flowed to the microheater 1 is increased to 3.5 mA to raise the measurement temperature T in a situation where each of the mixed gases is the ambient gas. It was confirmed from an experimental result depicted in FIG. 7 that the proportional relation between the heat radiation coefficient C and the thermal conductivity $\lambda_{(T)}$ of each of the mixed gases is maintained even when the measurement temperature T is changed, i.e., when the heater temperature is changed. Therefore, obtaining the proportional relation between the heat radiation coefficient C and the thermal conductivity $\lambda_{(T)}$ at the measurement temperature in advance enables accurately obtaining the thermal conductivity $\lambda_{(T)}$ of the mixed gas (the ambient gas) at the measurement temperature T in accordance with the heat radiation coefficient C acquired from the heater power Ph.

Moreover, it was confirmed from this experimental result that there is no error in analysis of the relationship between the heat radiation coefficient C and the thermal conductivity $\lambda$o of the ambient gas. That is, it was confirmed that there is no error in analysis performed when considering the average heat transfer coefficient h is in proportion to the thermal conductivity $\lambda$ of the ambient gas and in inverse proportion to the thickness d of the temperature boundary layer. Additionally, it was theoretically borne out that, even if the thermal conductivity (T) of the ambient gas at the measurement temperature T is obtained in accordance with the heat radiation coefficient C from the microheater 1, its measurement result has a sufficiently high accuracy.

Figure 8:
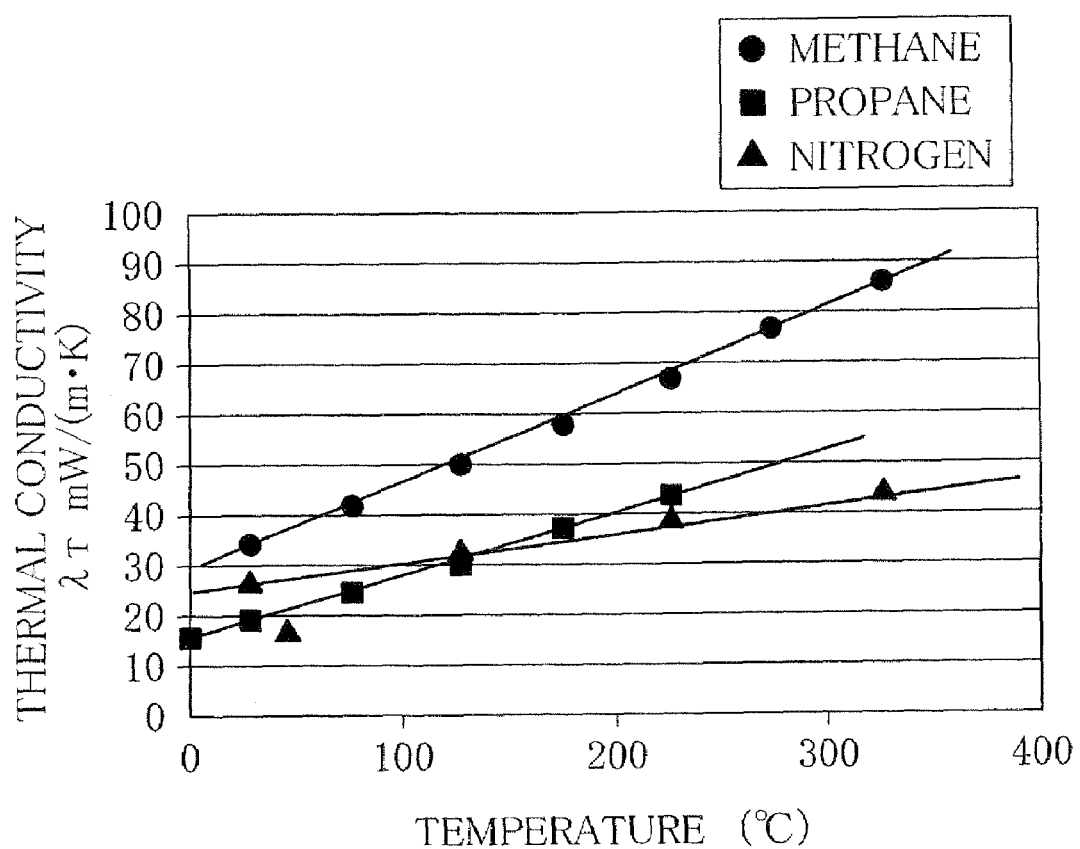
FIG. 8 is a view showing temperature characteristics of thermal conductivities $\lambda_{X(T)}$, $\lambda_{Y(T)}$, and $\lambda_{Z(T)}$ of a plurality of gases X, Y, and Z.

Meanwhile, when paying notice to a thermal conductivity of each of a plurality of types of pure gases, e.g., methane, propane, and nitrogen constituting a natural gas, the thermal conductivities $\lambda_{(T)}$ of these respective gases have different temperature change characteristics as shown in FIG. 8. Therefore, when the ambient gas is a mixed gas formed of the plurality of types of pure gases, the thermal conductivity $\lambda_{(T)}$ of the mixed gas varies depending on the temperature T even though composition ratios of the mixed gas remain the same. Therefore, when obtaining the thermal conductivity $\lambda_{(T)}$ of the ambient gas as explained above, setting, e.g., the measurement temperature T in advance is important. Alternatively, obtaining a relationship between the heat radiation coefficient C and the thermal conductivity $\lambda_{(T)}$ at each of various measurement temperatures T is required.

Additionally, conversely, this means that respectively obtaining thermal conductivities $\lambda_{(T1)}$, $\lambda_{(T2)}$, and $\lambda_{(T3)}$ of the ambient gas at; e.g., different temperatures T1, T2, and T3 enables back-calculating the composition ratios of the ambient gas from these thermal conductivities $\lambda_{(T1)}$, $\lambda_{(T2)}$, and $\lambda_{(T3)}$.

That is, when considering a mixed gas containing three types of pure gases X, Y, and Z (e.g., methane, propane, and nitrogen), assuming that mixing ratios of the respective gases (composition ratios of the mixed gas) are substantially x, y, and z, the thermal conductivity $\lambda_{(T1)}$ of the mixed gas at the temperature T1 is as follows:

$$x+y+z=1 \tag{12}$$

$$\lambda_{(T1)}=x \cdot \lambda_{X(T1)}+y \cdot \lambda_{Y(T1)}+z \cdot \lambda_{Z(T1)} \tag{13}$$

In this expression, $\lambda_{X(T1)}$, $\lambda_{Y(T1)}$, and $\lambda_{Z(T1)}$ are thermal conductivities of the respective gases X, Y, and Z at the temperature T1.

Likewise, the thermal conductivity $\lambda_{(T2)}$ of the mixed gas at the temperature T2 becomes as follows:

$$\lambda_{(T2)}=x \cdot \lambda_{X(T2)}+y \cdot \lambda_{Y(T2)}+z \cdot \lambda_{Z(T2)} \tag{14}$$

and, the thermal conductivity $\lambda_{(T3)}$ of the mixed gas at the temperature T3 becomes as follows:

$$\lambda_{(T3)}=x \cdot \lambda_{X(T3)}+y \cdot \lambda_{Y(T3)}+z \cdot \lambda_{Z(T3)} \tag{15}$$

Furthermore, since the thermal conductivities $\lambda_{X(T)}$, $\lambda_{Y(T)}$, and $\lambda_{Z(T)}$ of the respective gases X, Y, and Z have different temperature characteristics as explained above, the thermal conductivities $\lambda_{(T1)}$, $\lambda_{(T2)}$, and $\lambda_{(T3)}$ of the mixed gas obtained at the respective temperatures T1, T2, and T3 are different from each other.

It is to be noted that the thermal conductivities $\lambda_{(T1)}$, $\lambda_{(T2)}$, and $\lambda_{(T3)}$ of the mixed gas at the respective temperatures T1, T2 and T3 can be respectively obtained from the heat radiation coefficient C by, e.g., changing the energization current Th of the microheater 1 to gradually vary the heater temperature Th and thereby setting the plurality of temperatures T1, T2, and T3. Therefore, obtaining the heat radiation coefficients C under the respective measurement conditions while gradually varying the heater temperature Th enables acquiring each thermal conductivity (T) of the mixed gas at the reference temperature (the temperature T) that is set in accordance with the respective measurement conditions based on each heat radiation coefficient C.

Furthermore, temperature characteristics of the thermal conductivities $\lambda_{X(T)}$, $\lambda_{Y(T)}$, and $\lambda_{Z(T)}$ of the plurality of pure gases X, Y, and Z forming the mixed gas can be obtained in advance as shown in FIG. 8. Therefore, when the temperatures T1, T2, and T3 at which each thermal conductivity $\lambda_{(T)}$ of the mixed gas is obtained are determined, the thermal conductivities $\lambda_{X(T)}$, $\lambda_{Y(T)}$, and $\lambda_{Z(T)}$ of the respective gases X, Y, and Z at these temperatures T1, T2, and T3 can be obtained. Therefore, solving the mixing ratios x, y, and z as unknown numbers enables acquiring the composition ratios x, y, and z of the respective gases X, Y, and Z.

It is to be noted that the thermal conductivity $\lambda$ of the mixed gas is dependent on not only the composition ratios of the pure gases forming the mixed gas but also coupling coefficients F of the pure gases in a precise sense. Specifically, considering a mixed gas containing two types of pure gases X and Y (e.g., propane and nitrogen), assuming that thermal conductivities of the respective pure gases X and Y are $\lambda$x and $\lambda$y and mixing ratios of these gases (composition ratios of the mixed gas) are x and y, a thermal conductivity $\lambda$ of the mixed gas is as follows:

$$x+y=1 \tag{16}$$

$$\lambda=x \cdot \lambda x/(x+F_{xy} \cdot y)+y \cdot \lambda y/(y+F_{yx} \cdot x) \tag{17}$$

In this expression, $F_{xy}$ is a coupling coefficient of the pure gas X with respect to the pure gas Y, and $F_{yx}$ is a coupling coefficient of the pure gas Y with respect to the pure gas X.

Likewise, considering a mixed gas containing three types of pure gases X, Y, and Z (e.g., methane, propane, and nitrogen), assuming that thermal conductivities of the respective pure gases X, Y, and Z are $\lambda$x, $\lambda$y, and $\lambda$z and mixing ratios of the same (composition ratios of the mixed gas) are x, y, and z, a thermal conductivity λ of the mixed gas is as follows:

$$x + y + z = 1 \quad (16a)$$

$$\lambda = x \cdot \lambda x / (x + F_{xy} \cdot y + F_{xz} \cdot z) + \\ y \cdot \lambda y / (y + F_{yz} \cdot z + F_{yz} \cdot x) + z \cdot \lambda z / (z + F_{zx} \cdot x + F_{zy} \cdot y) \quad (17a)$$

In this expression, $F_{xz}$ is a coupling coefficient of the pure gas X with respect to the pure gas Z, $F_{yz}$ is a coupling coefficient of the pure gas Y with respect to the pure gas Z, $F_{zx}$ is a coupling coefficient of the pure gas Z with respect to the pure gas X, and $F_{zy}$ is a coupling coefficient of the pure gas Z with respect to the pure gas Y.

It is to be noted that the coupling coefficient $F_{ij}$ can be calculated based on, e.g., a Lindsay-Bromley's approximate expression as follows:

[Expression 1]

$$F_{ij} = \frac{1}{4}\left\{1 + \left[\frac{n_i^0}{n_j^0}\left(\frac{M_j}{M_i}\right)^{3/4}\frac{1+(S_i/T)}{1+(S_j/T)}\right]^{3/4}\right\}^2 \left[\frac{1+(S_{ij}/T)}{1+(S_j/T)}\right] \quad (18)$$

However, in the above expression, $n^0$ is a viscosity coefficient, M is a molecular weight, and S is a Sutherland constant. Further, a constant Si is given as [1.5 Tb] when Tb is determined as a boiling point, and a constant Sij is given as $[=(Si \cdot Sj)^{1/2}]$.

Therefore, using Expression (17a) in place of Expressions (13) to (15) and solving a simultaneous equation of the thermal conductivity λ obtained at each of different temperatures T enables accurately acquiring the composition ratios x, y, and z as unknown numbers.

In particular, when a mixed gas contains three types of gases as components thereof, since solving a cubic simultaneous equation enables obtaining component ratios of respective gases X, Y, and Z, acquiring thermal conductivities $\lambda_{(T1)}$ and $\lambda_{(T2)}$ at least at different temperatures T1 and T2 can suffice. Furthermore, in general, when temperatures T on [n–1] stages are set on the assumption that a mixed gas contains n types of gases, obtaining the thermal conductivity $\lambda_{(T)}$ of the mixed gas at each temperature T enables acquiring a composition ratio of each gas from an n-th degree simultaneous equation.

Figure 9:
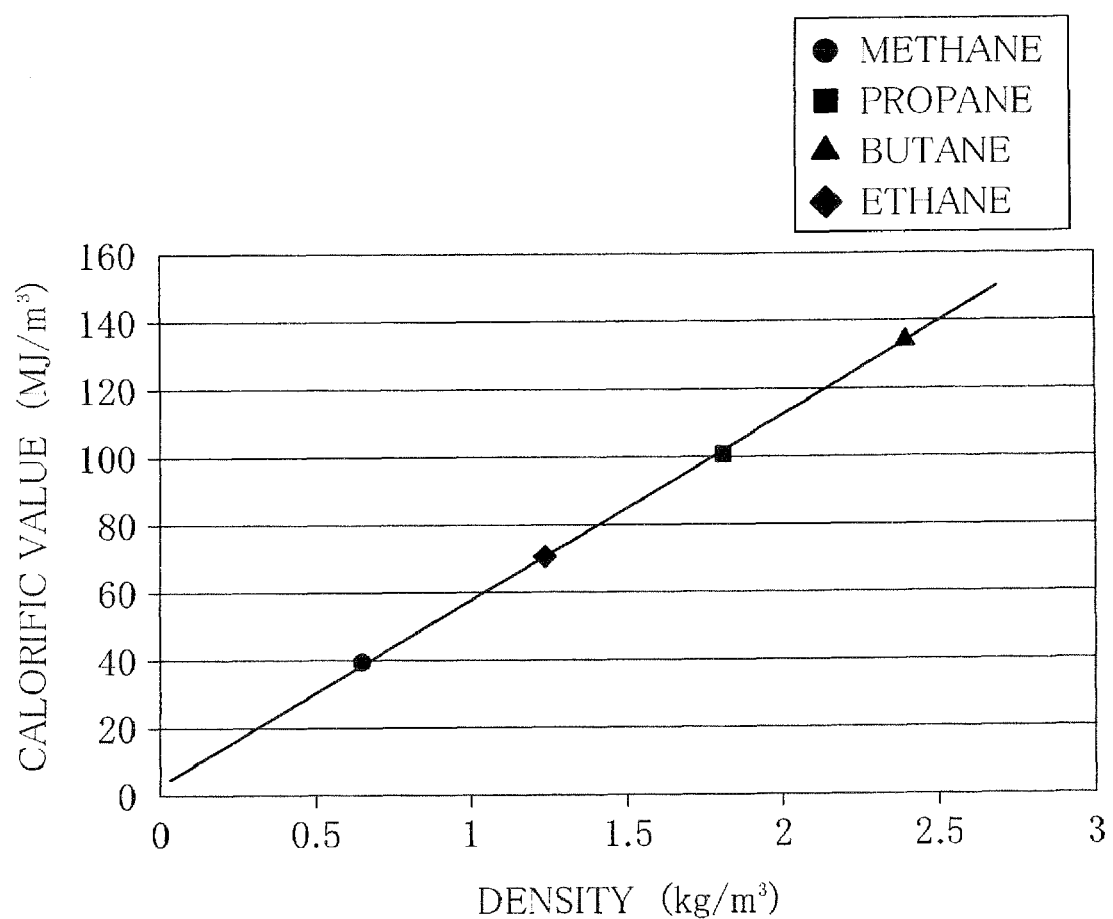
FIG. 9 is a view showing a relationship between a gas density and a calorific value.

Moreover, obtaining composition ratios of a plurality of gases forming a mixed gas as explained above enables acquiring a calorific value of each gas from the relationship between a gas density and a calorific value depicted in FIG. 9 in accordance with a total amount of the mixed gas and its composition ratios. Therefore, a calorific value of the mixed gas can be calculated. Specifically, a calorific value (an energy amount) of the mixed gas per unit volume can be readily and accurately calculated from component ratios obtained as explained above.

Figure 10:
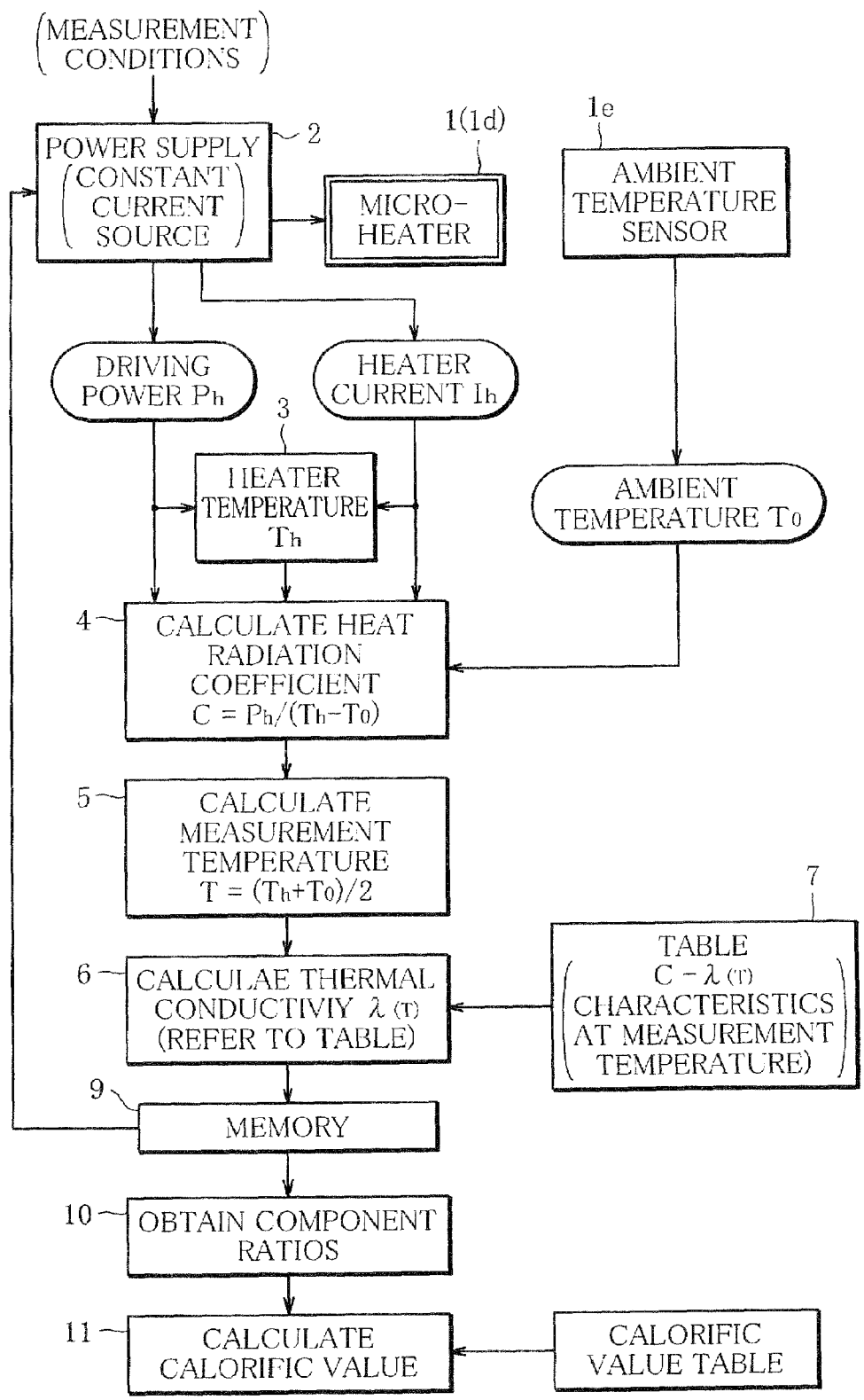
FIG. 10 is a view showing an outline structure of a gas component ratio measuring apparatus.
Figure 11:
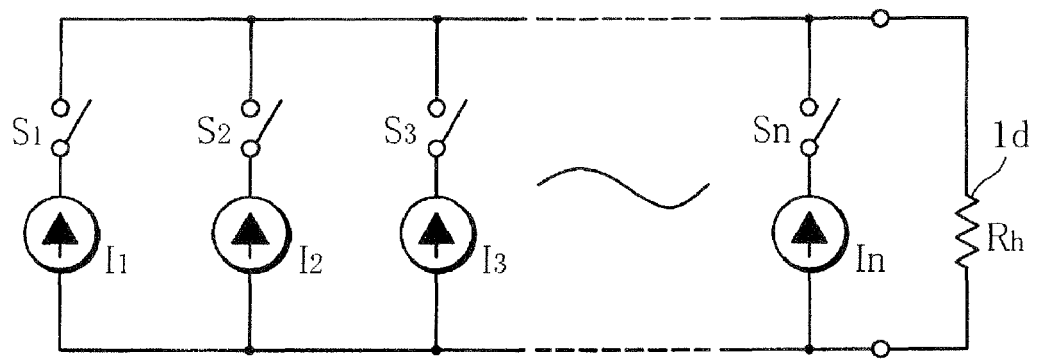
FIG. 11 is a view showing a structural example of a power supply.

A gas component ratio measuring apparatus which obtains component ratios of a mixed gas and also acquires a calorific value includes a memory 9 which stores a thermal conductivity $\lambda_{(T)}$ of the mixed gas at each temperature T and a thermal conductivity BUT of each of a plurality of gases which are considered to form this mixed gas at each temperature T in association with each other in addition to the thermal conductivity measuring apparatus depicted in, e.g., FIG. 10.

Additionally, the gas component ratio measuring apparatus is realized by including component ratio computing means 10 for setting up the simultaneous equation from the thermal conductivities $\lambda_{(T)}$ of the mixed gas and the respective gases stored in the memory 9 and analyzing this simultaneous equation to obtain a component ration of each gas, and calorific value calculating means 11 for calculating a total calorific value of the mixed gas in accordance with the component ratios obtained by this component ratio computing means 10. This calculation of the total calorific value is executed by making reference to, e.g., the relationship between a gas density and a calorific value in each gas type which is previously registered in a calorific value table 12 and depicted in FIG. 9.

It is to be noted that, when obtaining a thermal conductivity $\lambda o_{(T)}$ of an ambient gas in accordance with a heat radiation coefficient C while changing the driving power Ph (the heater current Ih) of the microheater 1, the power supply 2 that drives the microheater 1 to generate heat is realized as a constant current source that can vary its output current in accordance with measurement conductions for the ambient gas. Specifically, it is good enough for the power supply 2 to be realized as a device which includes a plurality of constant current sources I1, I2, and I3 to In and selectively connects these constant current sources I1, I2, and I3 to In with the microheater 1 through switches S1, S2, and S3 to Sn to drive the microheater 1 with a constant current.

According to the gas component ratio measuring apparatus having the above-explained structure, when gas components are already known like, e.g., a natural gas, component ratios can be readily obtained. That is, in case of a natural gas, its main gas components are methane, ethane, propane, butane, and others, and nitrogen or a carbon dioxide may be collaterally included in some cases. Therefore, when a thermal conductivity at each of a plurality of temperatures T is obtained to acquire a ratio of each gas component on the assumption that these respective gas components are all contained, a content ratio of a gas component which is not contained in a mixed gas is obtained as [0], thereby accurately acquiring mixing ratios of the gas components alone which are truly contained in the mixed gas. As a result, practically great effects, e.g., enabling evaluating a quality of a natural gas or readily monitoring a total calorific value of this gas can be demonstrated.

As explained above, according to the present invention, just obtaining a heat radiation coefficient C of the microheater enables accurately and easily acquiring a thermal conductivity $\lambda_{(T)}$ of a pure gas or a mixed gas. Further, a thermal conductivity λo of an ambient gas as a measurement target can be easily obtained without providing a large-scale facility, e.g., a constant-temperature bath like a conventional technology. Furthermore, changing a heater temperature Th to vary measurement conditions (a measurement temperature T) of the ambient gas enables accurately evaluating a thermal conductivity $\lambda_{(T)}$ according to the measurement temperature m irrespective of component ratios of a mixed gas.

Moreover, if a type of a mixed gas is known but component ratios of the same are unknown, obtaining a thermal conductivity $\lambda_{(T)}$ of the mixed gas when a heater temperature Th is changed enables accurately acquiring the component ratios based on temperature characteristics of a thermal conductivity $\lambda_{(T)}$ of each gas component. In particular, the component ratios can be readily and accurately obtained without using a complicated large-scale device like a gas chromatography. Additionally, when the gas component ratios of the mixed gas are obtained, practically great effects, e.g., enabling readily evaluating a total calorific value of the mixed gas in accordance with the component ratios can be demonstrated.

It is to be noted that the present invention is not restricted to the foregoing embodiment. For example, each arithmetic operation function in a heat transfer amount measuring apparatus can be realized by software in a microcomputer. Further, the structure of the microheater is not restricted in particular, and a heater element in an existing micro flow sensor can be adopted as it is. Furthermore, it is needless to say that heat generation driving means of the microheater 1 not restricted to the above-explained example.

Moreover, a temperature of the microheater 1 can be controlled while using a temperature sensor provided near the microheater 1 to monitor a temperature of an ambient gas heated by the microheater 1. When such a structure is adopted, a temperature distribution can be obtained based on a ratio of a heat generation temperature (a heater temperature Th) of the microheater 1 and a temperature of the heated ambient gas measured by the temperature sensor, and a thermal conductivity of the ambient gas can be evaluated based on this temperature distribution to adjust the heater temperature Th, thereby increasing a measurement accuracy of the thermal conductivity.

Figure 12:
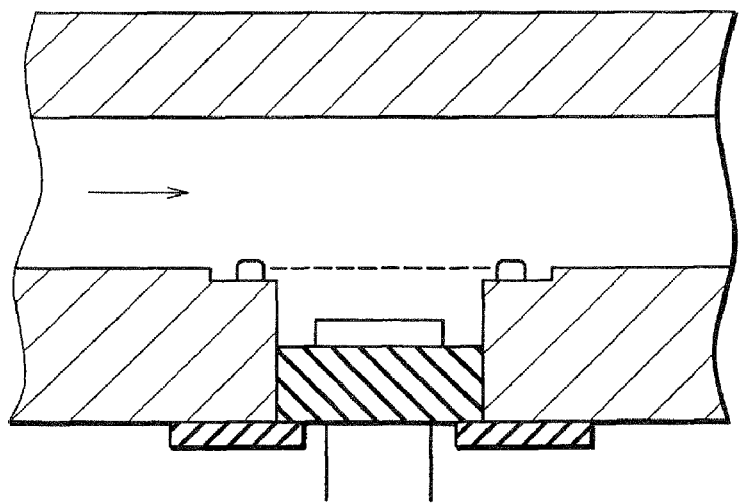
FIG. 12 is a view showing a structural example of a conventional thermal conductivity measuring apparatus.

Moreover, the present invention can be also applied to a technique of measuring a gas thermal conductivity in a constant-temperature bath in which an ambient gas is encapsulated as a background technology. In this case, since the ambient gas itself surrounding the microheater 1 is not substituted by any other gas, it can be said that a temperature Th of the microheater 1 achieves a thermal equilibrium state with the ambient gas. Additionally, the present invention can be also applied to such a thermal conductivity measuring apparatus using a cavity as shown in FIG. 12. In this case, since an ambient gas led to the cavity is stored and this gas is exchanged with an ambient gas flowing through a flow path by molecular diffusion alone, it can be considered that the ambient gas in the cavity and a heater enter a thermal equilibrium state when a driving power of the heater becomes fixed. Therefore, in this thermal equilibrium state, a thermal conductivity of the ambient gas can be highly accurately measured. Besides, the present invention can be modified in many ways without departing from the scope of the invention.

The invention claimed is:

1. A thermal conductivity measuring method using a microheater which is supported in air and provided in an ambient gas, the method comprising:
   calculating a heat radiation coefficient C=Ph/(Th−To) from the microheater in accordance with a power Ph applied to the microheater, a heater temperature Th, and an ambient temperature To at that moment; and
   obtaining a thermal conductivity $\lambda_{(T)}$ of the ambient gas from the calculated heat radiation coefficient C based on a proportional relation C=K·$\lambda_{(T)}$ between the thermal conductivity $\lambda_{(T)}$ of the ambient gas and the heat radiation coefficient C at a measurement temperature T, wherein K=(2/d)·(S), where d is a thickness of a temperature boundary layer of the ambient gas, and S is a heat radiating area of the microheater;
   wherein the thermal conductivity $\lambda_{(T)}$ is obtained based on the calculated heat radiation coefficient C by referring to a table in which the proportional relation between the thermal conductivity $\lambda_{(T)}$ of the ambient gas and the heat radiation coefficient C at the measurement temperature T is registered.

2. The thermal conductivity measuring method according to claim 1, wherein the measurement temperature T is obtained as an average temperature of the heater temperature Th and the ambient temperature To.

3. A thermal conductivity measuring apparatus comprising:
   a microheater which is supported in air and provided in an ambient gas;
   a heater temperature detecting section which obtains a temperature Th of the microheater;
   a temperature sensor which measures an ambient temperature To of the microheater;
   a power supply which energizes the microheater to generate heat;
   a heat radiation coefficient computing a heat radiation coefficient C from the microheater in accordance with an energization power applied to the microheater from the power supply, the heater temperature Th, and the ambient temperature To at that moment;
   a measurement temperature calculating section which obtains a measurement temperature T of the ambient gas in accordance with the heater temperature Th and the ambient temperature To; and
   a thermal conductivity computing section a thermal conductivity $\lambda_{(T)}$ of the ambient gas at the measurement temperature T from the heat radiation coefficient C calculated by the heat radiation coefficient computing section based on a proportional relation C=K·$\lambda_{(T)}$ between the thermal conductivity $\lambda_{(T)}$ of the ambient gas and the heat radiation coefficient C at the measurement temperature T, wherein K=(2/d)·(S), where d is a thickness of a temperature boundary layer of the ambient qas, and S is a heat radiating area of the microheater;
   wherein the thermal conductivity computing section obtains the thermal conductivity $\lambda_{(T)}$ based on the heat radiation coefficient C acquired by the heat radiation coefficient computing section by referring to a table in which the proportional relation between the thermal conductivity $\lambda_{(T)}$ of the ambient gas and the heat radiation coefficient C at the measurement temperature T is registered.

4. The thermal conductivity measuring apparatus according to claim 3, wherein the heater temperature detecting section calculates the heater temperature Th based on the following expression:

$$Rh = Rstd \cdot \{1 + \alpha(Th - Tstd) + \beta(Th - Tstd)^2\}$$

in accordance with a resistance value Rstd of the microheater at a standard temperature Tstd and a resistance value Rh of the microheater which is obtained from the following expression $$Rh = Ph/Ih^2$$

or from the following expression $$Rh = Vh/Ih$$

where Ih is an energization current Ih when the power supply energizes the microheater with the energization power Ph to generate heat, and where Vh is an end-to-end voltage of the microheater.

5. The thermal conductivity measuring apparatus according to claim 4, wherein the measurement temperature calculating section obtains the measurement temperature T as an average temperature of the heater temperature Th and the ambient temperature To.

6. The thermal conductivity measuring apparatus according to claim 4, further comprising a measurement condition changing section for changing the power Ph applied to the microheater to vary the heater temperature Th.

7. A gas component ratio measuring apparatus comprising:
an obtaining section which obtains a thermal conductivity $\lambda_{(T)}$ of an ambient gas at each of a plurality of different heater temperatures by using the thermal conductivity measuring apparatus according to claim 6; and
an analyzing section which analyzes composition ratios of the ambient gas based on a simultaneous equation of the thermal conductivity $\lambda_{(T)}$ at each of the heater temperatures.

8. The gas component ratio measuring apparatus according to claim 7, further comprising a calorific value obtaining section which obtains a calorific value of the ambient gas based on the composition ratios of the ambient gas acquired by the analyzing section.

9. The gas component ratio measuring apparatus according to claim 8, wherein the ambient gas is constituted of a natural gas mainly containing methane, ethane, propane, and butane.

10. The gas component ratio measuring apparatus according to claim 7, wherein the ambient gas is constituted of a natural gas mainly containing methane, ethane, propane, and butane.

* * * * *